United States Patent
Lamraoui

(10) Patent No.: US 10,531,944 B2
(45) Date of Patent: *Jan. 14, 2020

(54) SYSTEM FOR CONTROLLING AN IMPLANTABLE DEVICE ON THE BASIS OF COMMANDS ISSUED BY A USER

(71) Applicant: UROMEMS, Grenoble (FR)

(72) Inventor: Hamid Lamraoui, Grenoble (FR)

(73) Assignee: UROMEMS, Grenoble (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/899,198

(22) Filed: Feb. 19, 2018

(65) Prior Publication Data

US 2018/0193130 A1   Jul. 12, 2018

Related U.S. Application Data

(63) Continuation of application No. 14/378,938, filed as application No. PCT/EP2013/053469 on Feb. 21, 2013, now Pat. No. 9,918,821.

(Continued)

(30) Foreign Application Priority Data

Apr. 6, 2012   (FR) .................................... 12 53204

(51) Int. Cl.
A61F 2/02   (2006.01)
A61F 2/00   (2006.01)
(Continued)

(52) U.S. Cl.
CPC .............. *A61F 2/02* (2013.01); *A61B 5/0031* (2013.01); *A61F 2/0031* (2013.01);
(Continued)

(58) Field of Classification Search
CPC ........................................................ A61F 2/02
(Continued)

(56) References Cited

U.S. PATENT DOCUMENTS 4,619,245 A * 10/1986 Haber ................... A61F 2/0036
                                                    128/DIG. 25
5,830,912 A    11/1998 Gee et al.
(Continued)

FOREIGN PATENT DOCUMENTS

EP          1676543 A1     7/2006
JP          11-505445      5/1999
(Continued)

OTHER PUBLICATIONS

Wolpaw, Jonathan R., et al. "Brain-computer interfaces for communication and control." Clinical neurophysiology 113.6 (2002): pp. 767-791 (Year: 2002).*

(Continued)

*Primary Examiner* — Satish Rampuria
(74) *Attorney, Agent, or Firm* — Womble Bond Dickinson (US) LLP

(57) ABSTRACT

The invention relates to a system for controlling a device implanted in a human or animal body on the basis of voluntary commands issued by a user without the use of any external peripheral. The user issues a voluntary command to the implanted device by applying a specific and predetermined code, consisting of at least one mechanical action and of at least one additional piece of information. Each mechanical action and each additional piece of information are measured by at least one sensor. The output signal(s) of the sensor(s) are processed and used to validate the predetermined code by means of the identification of at least one mechanical action executed by the user and combined with at least one piece of additional information, and the com- (Continued)

parison thereof with a corresponding reference model. The invention further relates to a method for detecting an actuation control of an implantable device.

18 Claims, 11 Drawing Sheets

Related U.S. Application Data

(60) Provisional application No. 61/601,311, filed on Feb. 21, 2012.

(51) Int. Cl.
*A61B 5/00* (2006.01)
*A61N 1/36* (2006.01)
*A61N 1/372* (2006.01)
*G05B 13/04* (2006.01)
*A61F 2/48* (2006.01)

(52) U.S. Cl.
CPC ........ *A61F 2/0036* (2013.01); *A61N 1/36007* (2013.01); *A61N 1/37211* (2013.01); *G05B 13/04* (2013.01); *A61B 5/7475* (2013.01); *A61B 2560/0487* (2013.01); *A61F 2002/482* (2013.01); *A61F 2250/0002* (2013.01)

(58) Field of Classification Search
USPC ................................................ 700/275–306
See application file for complete search history.

(56) References Cited

U.S. PATENT DOCUMENTS

| | | | |
|---|---|---|---|
| 5,843,014 A | 12/1998 | Lattin et al. | |
| 6,471,635 B1* | 10/2002 | Forsell | A61F 2/0036 600/30 |
| 6,539,947 B2* | 4/2003 | Boies | A61B 5/0031 128/899 |
| 7,458,930 B2* | 12/2008 | Meretei | A61B 5/076 600/30 |
| 8,585,635 B2* | 11/2013 | Degen | A61M 1/285 604/29 |
| 9,205,255 B2* | 12/2015 | Strother | A61N 1/36007 |
| 2003/0199813 A1* | 10/2003 | Struble | A61B 5/0031 604/66 |
| 2003/0212306 A1* | 11/2003 | Banik | A61F 2/0036 600/30 |
| 2004/0111126 A1 | 6/2004 | Tanagho et al. | |
| 2004/0172087 A1* | 9/2004 | Forsell | A61F 2/0036 607/40 |
| 2006/0211913 A1* | 9/2006 | Dlugos | A61B 17/12099 600/37 |
| 2007/0060955 A1* | 3/2007 | Strother | A61N 1/36007 607/2 |
| 2007/0066995 A1* | 3/2007 | Strother | A61N 1/36007 607/2 |
| 2011/0306845 A1 | 12/2011 | Osorio | |

FOREIGN PATENT DOCUMENTS

| | | |
|---|---|---|
| JP | 2006-508768 | 3/2006 |
| WO | 96/30078 | 10/1996 |
| WO | 00/19939 A1 | 4/2000 |
| WO | 2010/040559 A2 | 4/2010 |

OTHER PUBLICATIONS

Lusted, Hugh S., and R. Benjamin Knapp. "Controlling computers with neural signals." Scientific American 275.4 (1996): pp. 82-87 (Year: 1996).*

Fernald, Kenneth W., et al. "A microprocessor-based implantable telemetry system." Computer 24.3 (1991): pp. 23-30 (Year: 1991).*

Pavithra, D., and Ranjith Balakrishnan. "IoT based monitoring and control system for home automation." 2015 global conference on communication technologies (GCCT). IEEE, 2015.pp. 169-173 (Year: 2015).*

McFarland, Dennis J., and Jonathan R. Wolpaw. "Brain-computer interface operation of robotic and prosthetic devices." Computer 41.10 (2008): pp. 52-56. (Year: 2008).*

Carrozza, Maria Chiara, et al. "A wearable biomechatronic interface for controlling robots with voluntary foot movements." IEEE/ASME Transactions on Mechatronics 12.1 (2007): pp. 1-11. (Year: 2007).*

Preliminary Research Report received for French Application No. 1253204, dated Dec. 3, 2012, 3 pages (1 page of French Translation Cover Sheet and 2 pages of original document).

International Search Report and Written Opinion received for PCT Patent Application No. PCT/EP2013/053469, dated Mar. 25, 2013, 18 pages (8 pages of English Translation and 10 pages of Original Document).

International Preliminary Report on Patentability received for PCT Patent Application No. PCT/EP2013/053469, dated Sep. 4, 2014, 13 pages (7 pages of English Translation and 6 pages of Original Document).

* cited by examiner

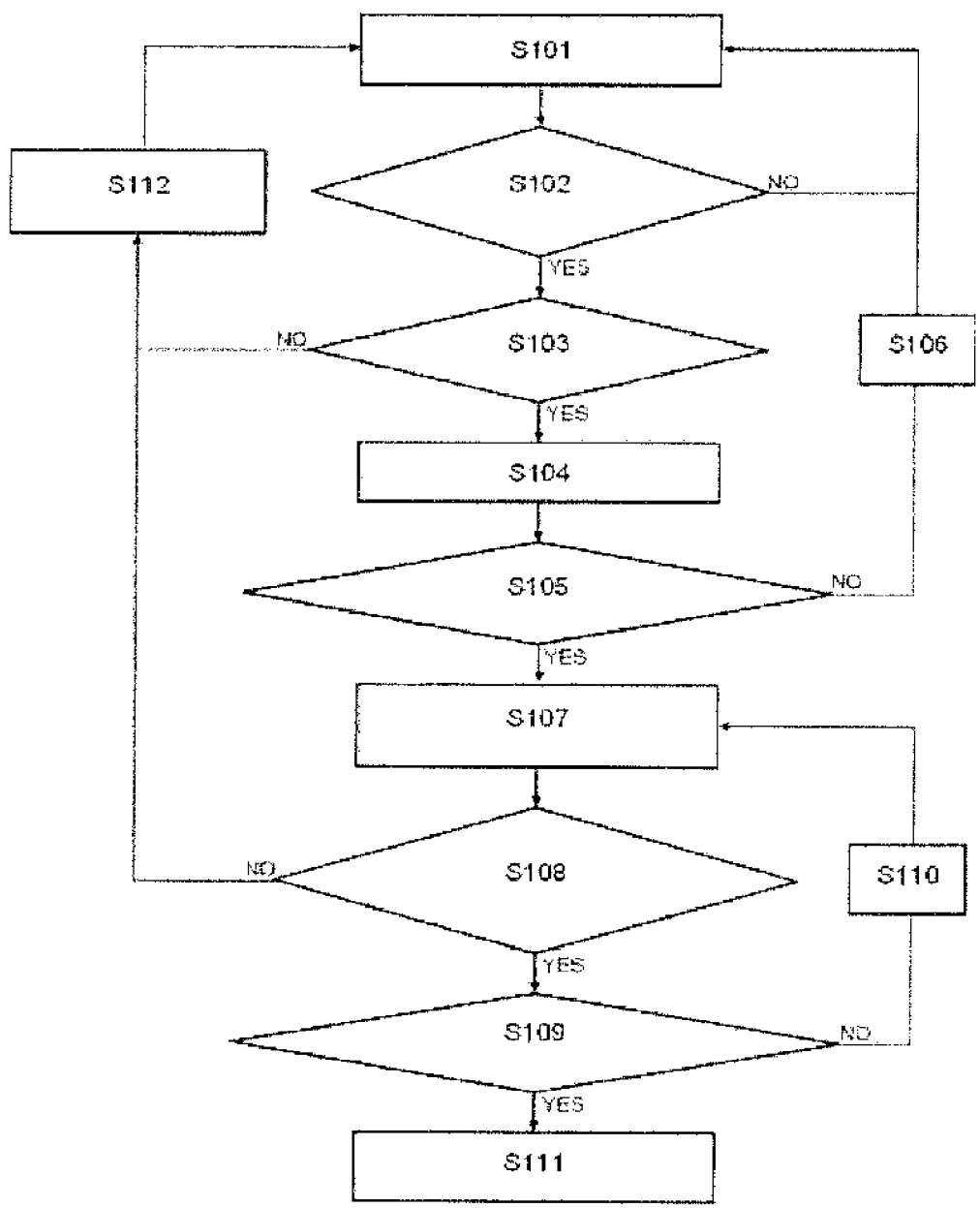

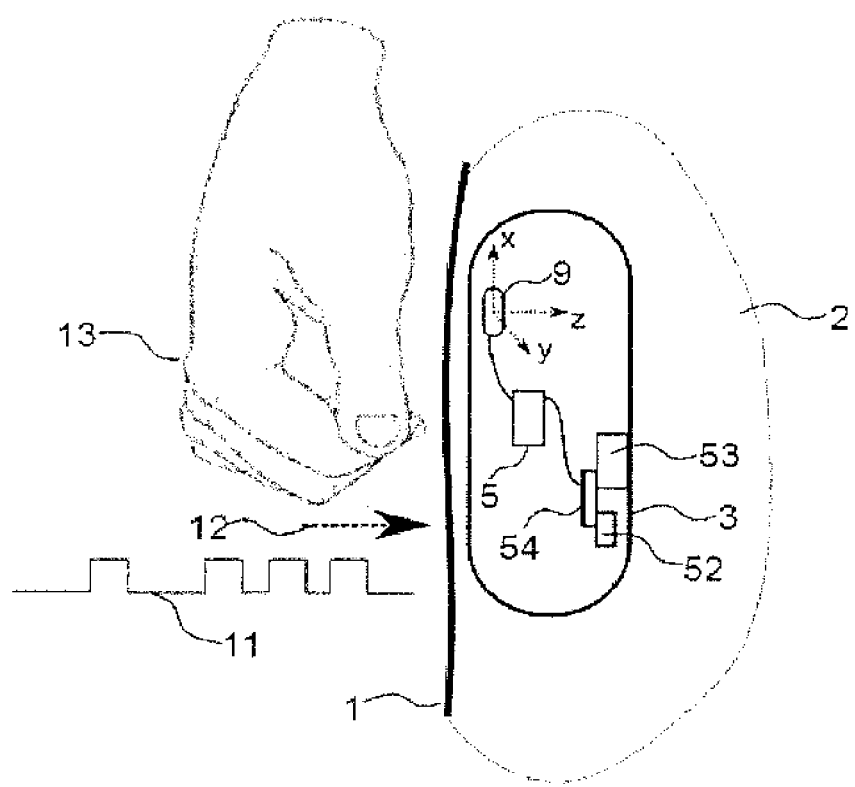

SYSTEM FOR CONTROLLING AN IMPLANTABLE DEVICE ON THE BASIS OF COMMANDS ISSUED BY A USER

FIELD OF THE INVENTION

The present invention relates in general to a system allowing the external control of an implantable device without any external device. This invention offers an ergonomic and safe medical implant control by the patient and the medical personal.

TECHNICAL BACKGROUND

Wireless communication, used in two different ways (induction and radiofrequency), is the common method for controlling and configuring battery-operated medical implantable devices. The configuration of the device requires an external wireless base connected to a control unit integrating a user interface. This procedure is commonly done by the physician in order to apply the right therapy for each patient. For some active implantable devices, the patient can control specific parameters bounded by the physician in order to partially modify the therapy. For instance, patients carrying an implantable pain control device can attenuate the pain thanks to a remote control. In the same manner, implantable neuromodulator of sacral nerve S3 for bladder stimulation can be controlled by the patient using an external device in order to activate or deactivate the implantable device or to modify the sacral nerve neurostimulation. A remote control can also be used by the patient for various medical implantable applications, for instance, the control of artificial sphincters, drug delivery system, neurostimulators or active gastric rings.

A drawback of this method is that the patient has to permanently carry the remote control. Since power supply is required in the remote control, autonomy has to be long enough to avoid to the user to be unable to perform wireless controls. Another disadvantage of this method is that in case of emergency, without an adapted remote device, it is impossible to control the active implant.

Control magnet is another way to control implantable device. By placing the magnet over the area where the implantable device is located, this can activate or deactivate the implantable device or some functions, or modify some parameters of the device.

Again, without the control magnet (and without an appropriate remote control) the user is unable to control the implantable device. Furthermore, when the patient is staying in electrically or magnetically noisy environments, random on or off switching of the implantable device or some of its functions may occur. If the patient lives or works in such environments, the magnet control has to be disabled by the clinician, thus depriving the patient of this feature.

The methods presented above have an obvious problem of ergonomics for the patient who has to carry permanently an object in order to control the device implanted in his body. Furthermore, in the case of a remote control, he has to be sure that the battery level of the remote control is sufficiently high to operate. Consequently, and in addition to the problem of ergonomics, this drawback can lead to a supplementary stress for the patient.

Problem of safety is another major drawback of these methods. In fact, without an appropriate device, the implantable device cannot be controlled in case of an emergency.

The object of the present invention is to provide a safe, reliable, simple and ergonomic solution for controlling an implantable device with the aim of resolving the above mentioned drawbacks.

SUMMARY OF THE INVENTION

In view on the above, it is an aim of the present invention to provide a method and a system for controlling, without any external object, a device previously implanted in a human or an animal body by sending orders to the device, and comprising the steps of:

applying to a part of the body comprising at least one previously implanted sensor a pattern of at least one mechanical action according to a predetermined code, the mechanical action being measured by at least one sensor and processed into at least one signal, wherein the predetermined code comprises at least one mechanical action defined by its corresponding at least one signal characteristics and at least one supplemental information detectable by at least one sensor, identifying each mechanical action in a portion of at least one signal measured and processed, comparing characteristics of each portion of at least one signal with a corresponding reference model of the signal characteristics, determining, from each signal comparison, whether all the measured mechanical actions actually belongs to the predetermined code, and if the applied pattern corresponds to a predetermined code, sending a corresponding predetermined order to the implanted device.

Corresponding reference model of the signal characteristics may be defined by the signal amplitude, statistical data, waveform or shape, frequency characteristics, duration, or any parameters that can describe a specific signal. Corresponding reference model of the signal characteristics may correspond to one or several characteristics of a signal which can be used to identify a specific signal.

In one embodiment, the detectable supplemental information comprises the absence, during a predetermined duration, of any mechanical action having an amplitude above a predetermined threshold.

In another embodiment, the detectable supplemental information comprises a predetermined posture during a predetermined duration.

Advantageously, the detectable supplemental information and each of mechanical action have a predetermined duration with predetermined lower and upper duration tolerances.

The supplemental information may be defined, depending of the sensor used, as being the output signal, or a parameter of the output signal, of at least one sensor's output signal below a predetermined threshold (hereafter referred to as "silence") and/or as corresponding to a specific posture of the patient, e.g. the patient is standing still or is lying down. Mechanical actions are detected when output signal(s) of the sensor(s) get over a predetermined threshold and when the signal(s) corresponding to the mechanical action have the same characteristics as a recorded reference model of the corresponding signal characteristics stored in a memory. An acceptable error on the comparison of the signal characteristics is considered.

In a preferred embodiment the method further comprises the steps of:

a) detecting at least one supplemental information in a portion of at least one signal that has a level below a predetermined threshold, b) detecting at least one mechanical action in a portion of at least one signal that has a level above a predetermined threshold during a period comprising a minimum and a maximum amount of time, corresponding respectively to a minimum and maximum mechanical action duration after a predetermined silence, c) storing each signal in a memory, d) repeating steps (a) to (c) for each portion of each signal until the end of the pattern to be detected, e) if the pattern does not correspond to a predetermined code, restarting to step (a) at any time until detecting a pattern corresponding to a predetermined code.

When a pattern corresponds to a predetermined code, each signal stored in memory is compared to its corresponding reference model of signal characteristics. If all the signals correspond to the expected mechanical actions measured by at least one sensor, the predetermined code is validated and a corresponding order is sent to the implanted device.

The corresponding reference model of the signal characteristics of each mechanical action may be updated periodically.

It is yet a further object of this invention to settle specific and predetermined codes of mechanical actions performed by a person and handled by an implantable control unit in order to make the implantable device to execute specific and predetermined orders corresponding to the code executed.

It is further an object of the present invention to measure the mechanical actions by employing at least one sensor previously implanted in the patient's body.

In a preferred embodiment, the predetermined order is selected from the group consisting of an activation or deactivation of the implanted device, at least one function activation or deactivation of the implanted device, a modification of at least one parameter of the implanted device, a modification of a therapy provided by the implanted device, a modification of the shape of the implanted device, and an activation or deactivation of a least one safety feature of the implanted device.

A feedback may be generated for the user when a predetermined order is sent to the implanted device.

Advantageously, the mechanical action is selected from the group consisting of external manual percussions over the sensor implantation site, muscular contractions, vibrations, pressure increase of a body cavity and pressure increase on the skin over the sensor implantation site.

The implanted device may be an artificial sphincter and predetermined order may comprise opening or closing an occlusive element of the artificial sphincter.

In a preferred embodiment, the implanted device comprises:

at least one sensor implantable in an animal or human body, and adapted for measuring mechanical actions, a control unit implantable in an animal or human body, and adapted for processing at least one signal coming from at least one sensor; detecting a predetermined code; identifying the mechanical action(s) in a portion of at least one signal measured; comparing characteristics of each portion of at least one signal with a corresponding reference model of the signal characteristics; determining, from the signal comparison, whether the measured mechanical action actually belongs to the predetermined code, and sending a predetermined order to the implanted device if the code is validated.

In a preferred embodiment, the sensor implanted in the patient's body is adapted to measure or to detect pressures, shocks, accelerations, vibrations or muscular contractions. The sensor may be selected from the group consisting of a 1-, 2- or 3-axis accelerometer, a gyroscope, a localization system, a pressure sensor and an electric commutator.

In a further embodiment, one or several of the sensors is not electrically supplied and generates an electrical signal when a mechanical action is applied on the sensor(s). The sensor may be a piezoelectric or a magnetic-based sensor.

The implantable device may be equipped with a wireless communication system between the implantable device and an external wireless base in order to configure the parameters of the predetermined codes detection.

It is to be noted that the method does not include the step of implanting the implantable device within the patient's body. Neither does it include the step of implanting any sensor or control unit if they are distinct from the implantable device itself.

The specific codes are made of at least one mechanical action executed by a person combined with at least one supplemental information detectable by at least one sensor and predetermined in order to be detected only when the person performs it and, consequently, to avoid untimely detection of the code.

Instead of using a remote control, patients and/or physicians may benefit of the method and apparatus of this invention to send themselves directly various types of orders to an implantable device.

In case of an artificial sphincter, the patient may control the opening and the occlusion of the artificial sphincter with one or two distinctive code(s). It would be also possible to adjust the degree of occlusion with a specific code.

In case of a neurostimulator, therapy may be modified by executing different codes according to the desired therapy.

More generally, functions of an implantable device may be, with predetermined codes, modified, deactivated, or activated.

Shape of an implantable device, such as gastric ring, artificial sphincter, orthopedic implant, may also be modified when a person executes a predetermined code of mechanical actions.

Another code may be implemented in order to disable the implantable device when desired.

In case of emergency, when no adapted external remote control is available to control the implantable device, an emergency code, known in every clinical center, could be executed by the medical personal in order to disable functions of an implantable device.

In a preferred embodiment, an automatic calibration routine is undertaken periodically in order to refresh the reference models of the signal characteristics of the mechanical actions. When a code is executed by a person the output signal(s) of the sensor(s) are recorded in memory. Characteristics are then corrected and recorded in memory to constitute a new model. The predetermined thresholds are also updated periodically in the same manner as the reference model of the signal characteristics of the mechanical actions. Detection parameters can be adjusted by an operator through a wireless communication between the implantable device and an external base.

An external device can also be used in order to reproduce the pattern of mechanical actions codes, in order far instance to configure the sensitivity of detection system.

The invention also relates to a detection method of an activation command of an implantable device by a user, likely to be used in the system described above.

More precisely, said detection method comprises the following steps:

- receiving from one or more sensors of the device a command signal comprising a sequence of values, some values being representative of mechanical actions exerted voluntarily by the user on the sensor and other values being representative of additional information such as a period between two successive mechanical actions exerted on the sensor or sensors,
- receiving from a memory of the device one or more reference signals,
- estimation of a similarity index by comparison of at least one portion of the command signal with at least one portion of the reference signal,
- if the similarity index is greater than a threshold value, recognition of a predetermined activation code of the device.

If said predetermined code is recognized, an activation order of the device can be sent.

BRIEF DESCRIPTION OF THE DRAWINGS

FIG. 11 is a flow chart illustrating all the required steps for the validation by the control unit of a code of combined mechanical actions executed in a predetermined way by a person. When a predetermined code is validated, the control unit sends a corresponding command to the implantable device.

FIG. 12 shows a configuration of the detection system of mechanical actions executed by a person where the sensors are a 3-axis accelerometer electrically supplied and a piezoelectric sensor not electrically supplied. In this configuration, the mechanical actions are acceleration, or more generally vibrations (e.g. muscular contractions, abdominal movements . . . ) purposely initiated by the user. When a vibration is sufficiently high, over a predetermined threshold, an electrical signal is generated by the piezoelectric sensor and is sent to the control unit in order to wake up the control unit and the 3-axis accelerometer, previously in a sleep mode and in order to initiate the detection phase.

DETAILED DESCRIPTION OF PREFERRED EMBODIMENTS

Figure 1:
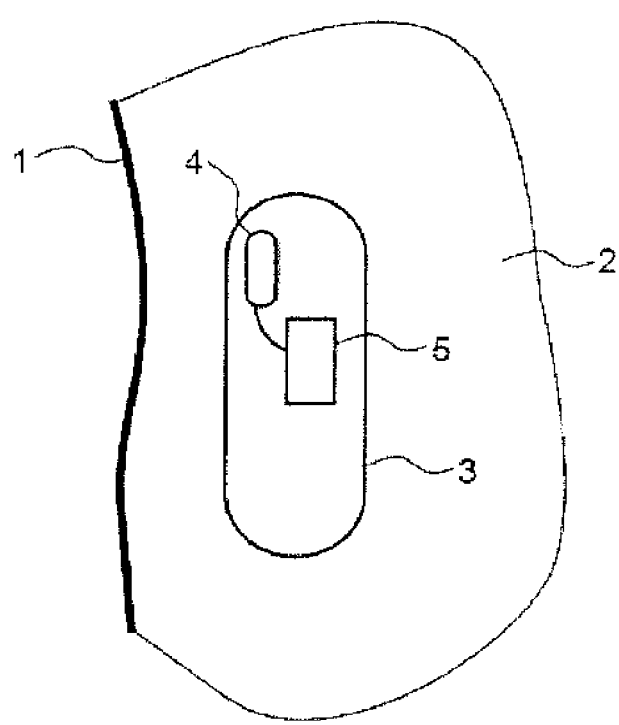
FIG. 1 illustrates one configuration of the detection system of mechanical actions executed by a person. In this configuration, the sensor unit and the control unit are embedded inside the implantable device housing. The control unit can be the control unit of the implantable device handling the detection method of mechanical actions executed in a predetermined code by the user.

The present invention is preferably implemented in an implantable device with the purpose of controlling the implantable device without using any external device and with the purpose of offering an ergonomic and safe solution for the control of the device. The user either can be the person who carries the implantable device or an external person. In order to send a command to the implantable device, the user has to execute a predetermined code of mechanical actions that can be discriminated by a control unit as the specific command among all the data measured by the sensor(s) in the daily activities of the person who carries the implantable device.

The present invention may be employed in various applications. For purpose of illustration, the present invention will be described in the context of Implantable Medical Devices (IMD) such as pacemakers, defibrillators, neuromodulators, artificial sphincters, gastric rings or infusion pumps.

Many functions of an IMD may be controlled by employing the present invention. The IMD may be activated or deactivated entirely (i.e. device switched on or off respectively) or partially (i.e. only some functions of the IMD). This function may find utility in IMD such as neuromodulators for which the therapy can be temporarily stopped by the patient in order to increase the lifetime of the IMD, by reducing the power consumption when the therapy is not needed. For instance, in the case of the sacral neurostimulation, the patient could turn off the IMD without any external remote control.

The present invention may also be employed in order to offer to the medical personal a deactivation of the IMD in case of emergency.

The present invention may also be employed for IMD for which the therapy can be adjusted.

Artificial sphincter is another interesting IMD application for which the present invention may be employed. In the case of artificial urinary sphincter, to trigger the micturition (i.e. to open the occlusive cuff), the patient executes a predetermined code of mechanical actions. Another code may be used to stop the micturition (i.e. to close the occlusive cuff). More generally, the present invention may be employed to modify the shape of an IMD such as gastric band or artificial prosthesis, to control safety features of an IMD, such as emergency stop or emergency therapy, to modify one or more parameters of the IMD, such as therapy parameters, or finally wake up or asleep one or more functions of the IMD.

The IMD implementing the present invention is equipped with one or more appropriate sensors able to measure patterns of mechanical actions which may preferably be pressures, shocks, accelerations, movements, vibrations or muscular contractions. The kinds of sensors which may be used are preferably pressure sensors, commutators, gyroscopes, or accelerometers with at least one axis. Another method to measure indirectly mechanical actions initiated by muscular contractions may be the electromyography commonly employed to measure the muscular activity. Finally, positioning systems (global positioning systems or local positioning systems) may be used to measure variations of position related to the mechanical actions.

In order to implement the present invention, a control unit has to be implemented for acquiring, conditioning, storing and processing data coming from the sensor(s). This control unit may be especially dedicated for the prevent invention or may correspond to the control unit of the IMD handling the data coming from the sensor(s) mentioned above.

FIG. 1 to FIG. 7 illustrate preferred hardware configurations for implementing the present invention. Various hardware configurations are possible depending on the implantation site of the IMD and depending on sensor(s) used to measure the mechanical actions. Furthermore, depending of the nature of the mechanical actions, the implantable parts (sensor(s), control unit and IMD) have to be placed in a way that will maximize the detection quality of the present invention.

For purpose of illustration, there is only one sensor represented on FIG. 1 to FIG. 7. It has to be understood that more than one sensor can be implemented with a hardware configuration of each sensor preferably described on one of the FIG. 1 to FIG. 7.

In FIG. 1, the sensor 4 and the control unit 5 are embedded in the IMD 3 implanted inside a body cavity 2 under the skin 1. In this configuration the nature of the mechanical actions is preferably shock, vibration or acceleration generated either on the skin of the patient or by muscular contractions. Regarding the control unit, it can be the control unit of the IMD handling the detection method of mechanical actions executed in a predetermined code by the user.

Figure 2:
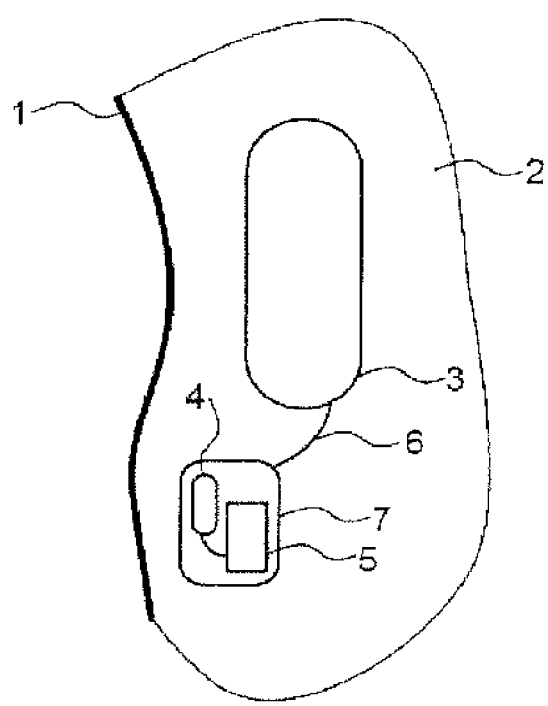
FIG. 2 illustrates another configuration of the detection system of mechanical actions executed by a person. In this configuration, the sensor unit and the control unit are still implanted but are embedded inside a dedicated housing communicating through either a wired or wireless communication with the implantable device.

In FIG. 2, the sensor 4 and the control unit 5 are embedded inside another implantable housing 7 in order to be placed inside a body part where it is not suitable for the IMD. In this case, the control unit communicates through a wired or wireless communication 6 with the IMD. The communication is bidirectional in order to send and receive data in both terminals. In this hardware configuration, any of the mechanical actions nature may be sensed, depending on the sensor employed.

Figure 3:
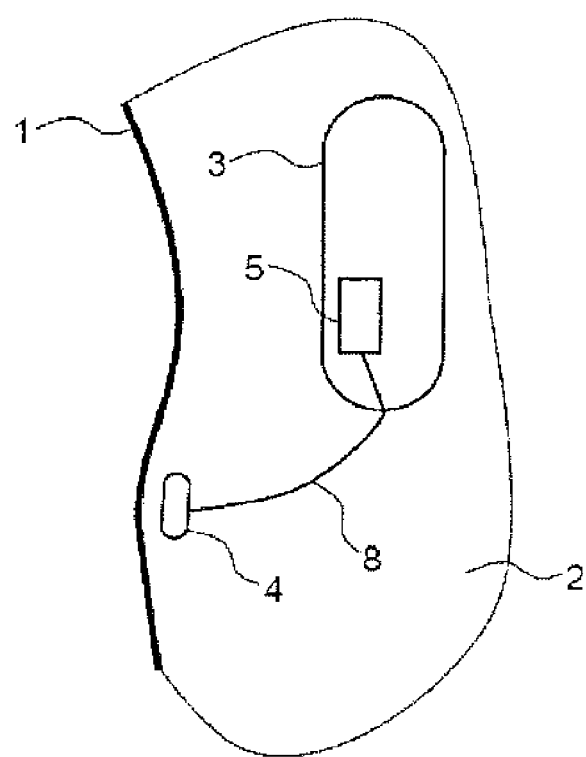
FIG. 3 illustrates another configuration of the detection system of mechanical actions executed by a person. In this configuration, only the sensor unit is embedded inside a dedicated housing communicating through either a wired or wireless communication with the implantable device. The control unit can be the control unit of the implantable device handling the detection method of mechanical actions executed in a predetermined code by the user.

FIG. 3 illustrates the same configuration, except that the control unit 5 is embedded inside the IMD 3. This configuration may be useful if the space where the sensor 4 is implanted is restricted. The sensor has an implantable housing and communicates with the control unit 5 placed inside the IMD 3 through a wired or wireless communication 8. The control unit can be the one of the IMD handling the detection method of mechanical actions executed in a predetermined code by the user.

The following description presents preferred but non limitative embodiments of the invention. Sensors are defined above but are not limited to the one cited. They can be replaced by any sensor able to measure the same kind of mechanical action.

The hardware configurations represented in FIG. 4 to FIG. 7 are illustrated with the sensor and control unit embedded in the IMD. It has to be understood that hardware configurations mentioned above and represented in FIG. 2 and FIG. 3 may be employed.

Figure 4:
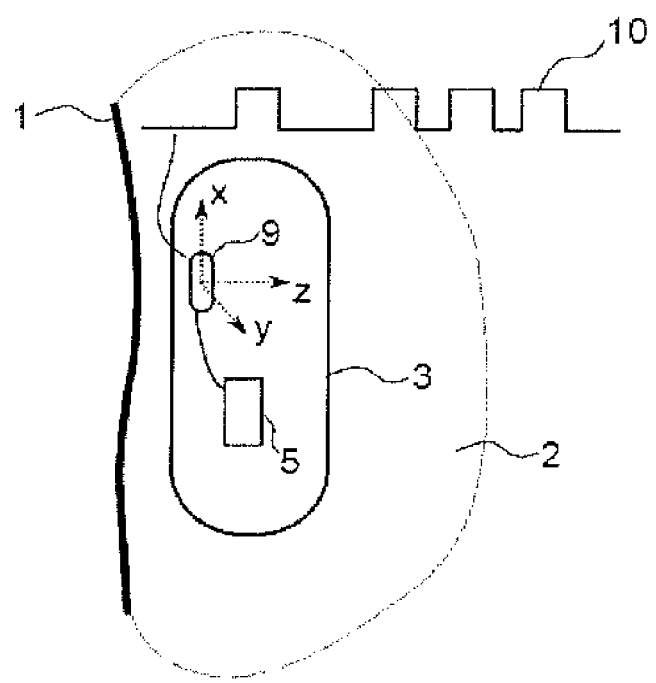
FIG. 4 shows a configuration of the detection system of mechanical actions executed by a person where the sensor unit is a 3-axis accelerometer. In this configuration, the mechanical actions are acceleration, or more generally vibrations (e.g. muscular contractions, abdominal movements . . . ) purposely initiated by the user.
Figure 5:
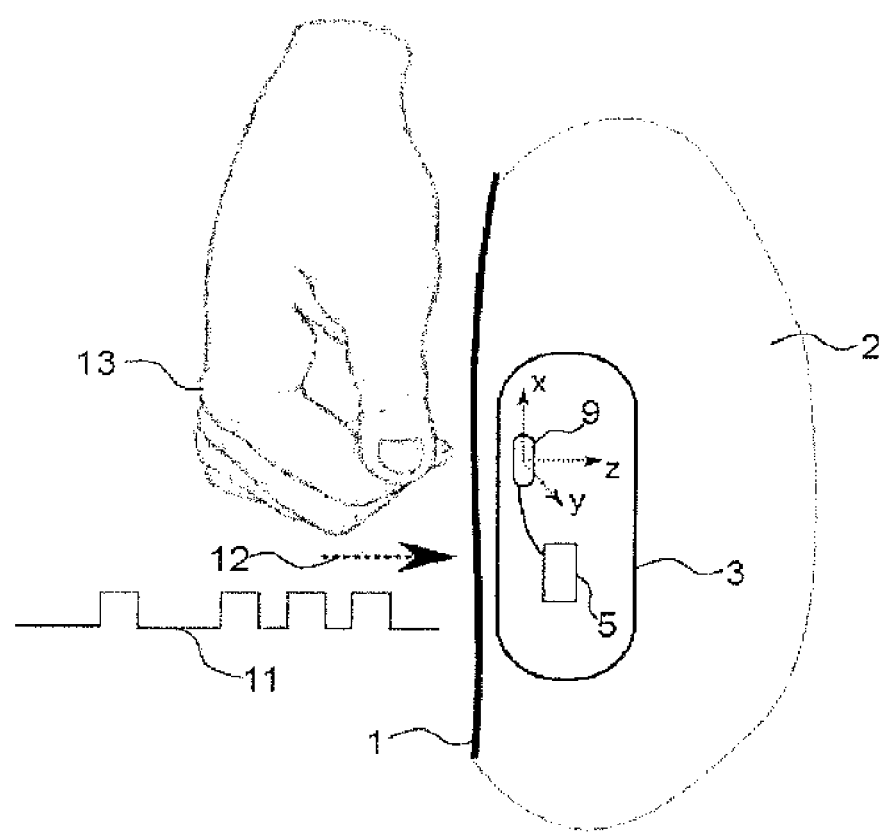
FIG. 5 is an illustration showing the control of the implantable device by hand tapping. In this configuration, the user executes a code by tapping on the skin, over the implantation site of the sensor unit, in order to send a command to the implanted device.

One preferred configuration is described on FIG. 4 and FIG. 5.

The sensor in this hardware configuration is a 3-axis accelerometer 9 measuring accelerations of the IMD 3.

A predetermined code 10 of shocks or vibrations is illustrated on FIG. 4. It consists of one silence followed by one mechanical action then one new silence followed by three mechanical actions separated by short silences. In this configuration, the mechanical action may be voluntary muscular contractions inducing vibrations or shocks inside the body cavity 2 where the IMD 3 is located. On FIG. 5, the shock measured by the 3-axis accelerometer in order to detect the predetermined code of mechanical actions 11 is performed externally. The user applied with his hand 13 the predetermined code by tapping on the skin 1 (or in any case over the implantation site of the IMD including the sensor), in the direction 12 of the IMD 3 and where the IMD is located. The code 11 represented on FIG. 5 corresponds to one silence followed by one hand tap on the skin 1, then one new silence followed by three taps on the skin separated by short silences. In both case illustrated by FIG. 4 and FIG. 5, the signals sent to the control unit are the three signals coming from the X, Y and Z axis acceleration measures of the accelerometer in order to have the most accurate signature of the mechanical action.

It has to be understood that an accelerometer with only one or two measure axis may be used if the signature of the mechanical action is sufficiently accurate with one or two signals) coming from the accelerometer.

In the case of the accelerometer, the silences may be defined by a dynamic acceleration or a parameter of dynamic acceleration below a predetermined threshold which may be combined with a specific posture. For example, in the case of an implantable artificial urinary sphincter, the micturition may be controlled by the patient by employing the present invention. To trigger the opening of the artificial urinary sphincter, the patient will have to tap with his hand on the skin where the artificial sphincter sensor is located as described above. The silences in this case correspond to the patient still, in quasi-immobile position, with his trunk in a vertical position. In this posture, and when the patient does not move, the output signals coming from standard micro-machined accelerometer consisting of a proof mass suspended by springs (for example, the ADXL335 sensor marketed by the company Analog Devices), have an AC component (i.e. "dynamic" acceleration) with a low level. The DC component (i.e. "static" acceleration) of each measure axis may be used to define the posture of the patient thanks to the measure of the gravity component.

Figure 6:
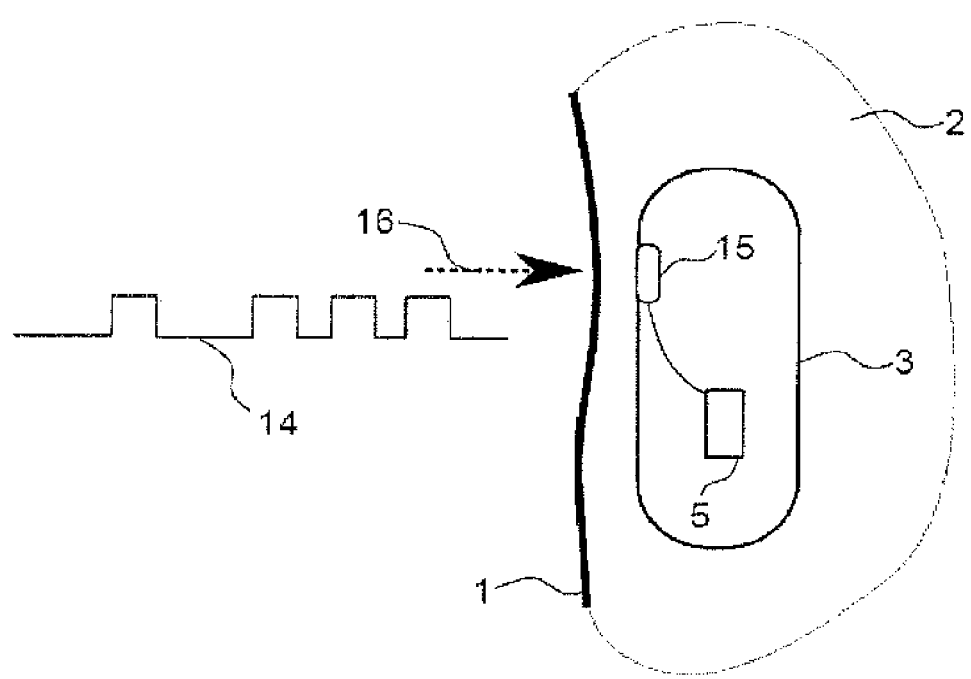
FIG. 6 is an illustration showing the control of the implantable device by applying pressure on the skin. In this configuration, the user executes a code by applying pressure on the skin, over the implantation site of the sensor unit (based on a pressure sensor), in order to send a command to the implanted device.
Figure 7:
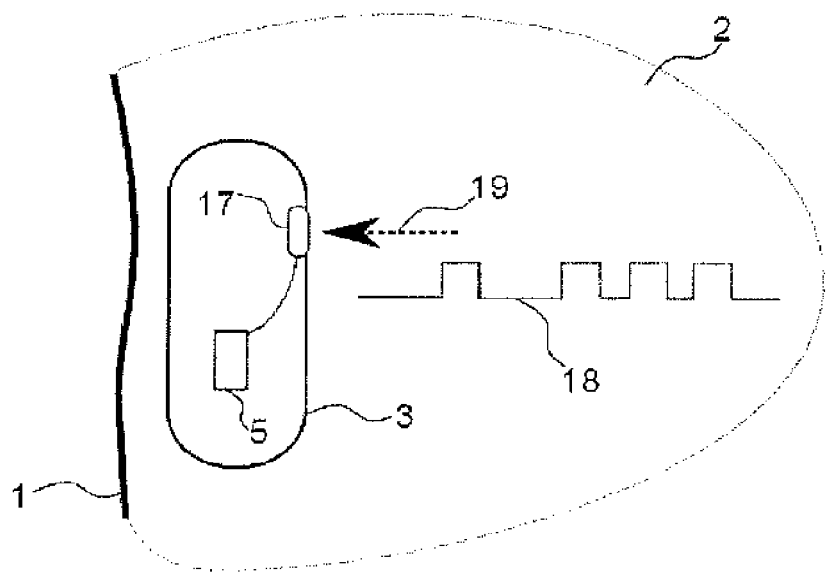
FIG. 7 is an illustration showing the control of the implantable device by voluntarily applying pressure inside the human body. In this configuration, the user executes a code by generating a pressure inside a body cavity (e.g. abdominal cavity), where the sensor unit is located, in order to send a command to the implanted device.

FIG. 6 and FIG. 7 depict a hardware configuration designed for measuring pressure on the housing of the IMD (or the housing of the detection unit if it is deported of the IMD). In a preferred embodiment, the sensor 15, 17 is a pressure sensor or a commutator for which the output signal varies according to the pressure applied on it. It may also be a hydraulic or pneumatic sensor connected to a balloon generating a pressure when it is deformed. In FIG. 6, the sensor 15 is placed in a way that pressure applied on the skin 1 can be measured. The pressure is applied in the direction represented by the arrow 16. A predetermined code 14 consisting of pressure exerted on the skin (e.g. with the hand of the user) combined with silences is detected by the sensor 15 and the control unit 5. The silences in this configuration are defined as the output signal of the sensor or a parameter of the output signal under a predetermined threshold (low pressure applied on the skin). The same configuration is illustrated on FIG. 6 except the sensor 17 is placed so that the pressure is measured inside the body cavity 2. The pressure is measured mainly in the direction represented by the arrow 19. The pressure in this case may be generated by contractions of the muscles surrounding the space 2 where the IMD 3 is located. The predetermined code 18 respects the same constraint of the code 14 defined above and represented on FIG. 6.

A combination of sensors for measuring mechanical actions or silences of different types can also be implemented. For example, in the case of tapping on the skin, the device can implement the combination of acceleration measuring (measured by an accelerometer) and pressures (measured by a sub-cutaneous pressure sensor).

Preferred hardware configurations have been described in the last paragraphs above.

It is important to set a good hardware configuration in order to have, depending on the mechanical action that is employed, the best measure, and thus the possibility to collect accurate data.

In the next paragraphs, the procedure and the method allowing acquiring and processing the data collected are described.

Without a suitable acquiring and processing method, the predetermined code of mechanical actions cannot be detected at each time it is executed by the user. On the other hand, the method has to be sufficiently specific to provide a reliable solution allowing to detect the codes only when they are executed but not by error due to parasitic signals (e.g. undesired movements of the patient, breathing, undesired pressure applied on the skin or undesired muscular contractions) measured by the sensor and processed by the control unit. In order to offer a reliable solution and to avoid false detections of a code, theses aspects are taken into account in the present invention and described in the next paragraphs.

As said above, the predetermined code consists of mechanical actions combined with at least one supplemental information detectable by said at least one sensor, e.g. periods of silences, Silences are defined depending of the sensor employed as processed output signal(s) with a low amplitude level. A threshold is used to determine if the processed output signal(s) conditioned by the control unit has a level sufficiently low and correspond to a silence. In certain conditions, other information such as the position or the posture of the patient who carries the IMS, or else a specific parameter of silence may be used in order to increase the reliability of the detection.

Figure 8:
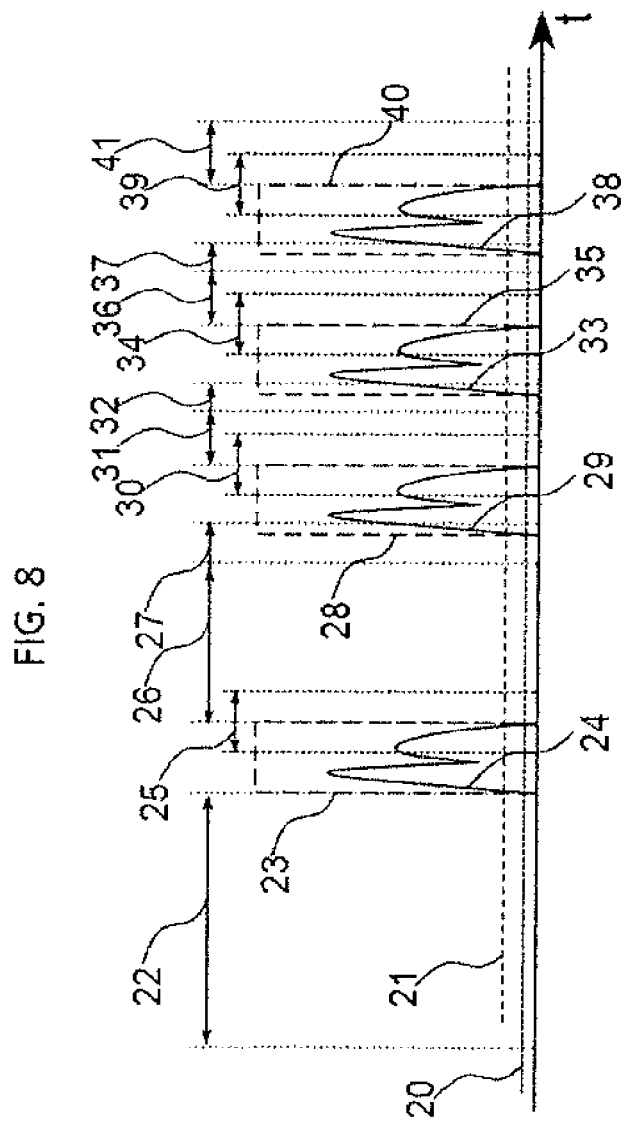
FIG. 8 illustrates the time criteria which have to be filled in order to validate the first step of the code detection. The code consists of several signal "silences" corresponding to a signal level below a predetermined threshold and several mechanical actions corresponding to a signal level over a predetermined threshold.

The hardware configuration as represented on the FIG. 5 is used in this paragraph for purpose of illustration. Only the accelerations along the Z axis of the accelerometer 9 are measured. The graph represented on the FIG. 8 illustrates the output signal of the accelerometer corresponding to the measure of the acceleration along the Z axis (along the direction showed by the arrow 12). The output signal is band-pass filtered in order to have only the AC component (i.e. the dynamic component) of the acceleration and to remove the high-frequency noise, then rectified for finally extract the envelope. The DC component, not represented on FIG. 8, may also be used in order to know roughly the posture of the patient (around 0 g when the patient has his trunk in a vertical posture and around ±1 g when he has his trunk in a horizontal position if the IMS is located in this part of the human body). The waveforms 24, 29, 33 and 38 correspond to the signal measured by the sensor and processed by the control unit when the user executes a hand tapping on the skin, over the implantation site of the device. The time periods of silence corresponds in this configuration to the processed output signal (or else one of the parameters of the signal) to a signal level below the threshold 20. Additionally, in some application, it may be possible to make the code detection more robust and reliable by using the DC output signal of the accelerometer in order to have an estimation of the posture of the patient. The time slots 23, 28, 35 and 40, combined with the silences, represent a typical code executed, respecting time requirements. Time tolerances are implemented on the mechanical actions duration as well as on the silences. When a mechanical action is detected, in the case illustrated, when the process signal is over the threshold 21, the mechanical actions executed in the time slot 23, 28, 35 and 40, have to respectively end (i.e. signal level below the threshold 20) within the time window 25, 30, 34 and 39 in order to be validated. The code presented in FIG. 8 consists of four mechanical actions (hand tapping) and five time periods of silence. In order to validate the code the user has to respect a minimum time period of silence 22 followed by a mechanical action, then a new time period of silence followed by three mechanical actions separated by short time period of silences. Finally, at the end of the last mechanical action, a minimum time period of silence 41 have to be respected. During all the period of code execution, the user does not move the body part where the IMD is implanted. Time constraints are also defined for each period of silence. In the case of the first and the last silence periods, only a minimum time period constraint has to be respected. Regarding the silence periods separating the mechanical action period, specific predetermined minimum periods 26, 31, 36 are also defined. Another constraint during these silences is the maximum time periods 27, 32, 37. A maximum period of time may also be defined for the first silence depending of the targeted application.

For each order, each duration constraint, number of silences and number of mechanical actions mentioned above are defined in order to determine a specific and predetermined code. The mechanical actions may not be necessary the same in the same code. All the parameters may be adjusted by the physician in order to convene to each patient. This can be performed by a parameterization through the wireless communication between the IMD and an external base. Both of the terminals have to handle bidirectional communication in order to set the implantable device properly.

In order to have a robust and a reliable detection method, the predetermined codes of mechanical actions cannot be simply detected by means of a simple exceeding of the threshold of amplitude level of the signal and time delay constraints. In fact, the system measures mechanical actions in the daily activities of the patient. The code detection procedure has consequently to be very robust in order to avoid false detection of a code by measuring a pattern of mechanicals actions which, after signal processing, have the same characteristics in term of delays and amplitude levels requirement, as stated above, of a predetermined code. Thus, among all the data collected by the measuring system all along the lifetime of the implantable device, actuals codes executed by the user have to be identified precisely and only in this situation. Furthermore, if the present invention is used for IMD applications, false detection or non-detection related to some orders, such as emergency stop or therapy modification can be critical for the patient. It is then very important to provide a reliable solution allowing the detection of a code only and only when it is properly executed.

In addition to the acquisition procedure described with reference to FIG. 8, the method also comprises a validation procedure of the predetermined code.

FIG. 11 is a block level diagram illustrating each step that can be executed before validating the order.

The nomenclature of the blocks, the content of which is explained in detail hereinbelow, is the following:
S101: Acquisition of sensor data
S102: Mechanical action or silence detected?
S103: Predetermined delays respected?
S104: Storing sets of data i
S105: i=number of mechanical actions and silences to be detected?
S106: i=i+1
S107: Comparison of the set of data j with a reference model
S108: Correspondence of the set of data j with the reference model?
S109: j=number of mechanical actions and silences to be validated?
S110: j=j+1
S111: Sending the order associated with the command to the implantable device
S112: Cancellation of stored sets of data if there are any, i=0, j=0.

The steps S101 to S106 and S112 correspond to the procedure stated above and illustrated by FIG. 8. It is the first stage of the method. During the step S101, data are measured continuously, per period or by using adaptive methods offering the possibility to measure data only when it is necessary (e.g. non uniform sampler) in order to minimize the IMD power consumption. The index i corresponds to the number of mechanical actions and silences to be detected in the code. If multiple predetermined codes are programmed, the maximum number of index i can be modified by the control unit during the detection procedure according to the time delays that must be respected. In others words, during the step S103, time periods of mechanical actions and silences listed in the memory according to the index (depending of the lasts mechanical actions and silences already executed) are compared to the last one measured in order to know which programmed code can be took into account. If it does not correspond to any of the time periods of mechanical actions and silence listed, the system goes to the step S112, otherwise the index is incremented (step S106) and the predetermined code references which can potentially be the one to be detected are stored in memory. The first procedure of the method is repeated until one code is detected. The validation procedure constitutes a second stage of the method, represented by steps S107 to S112. The control unit will apply, for each saved set of data in the first stage, corresponding to one mechanical action or silence (supplemental information), a comparison to an associated reference model stored in memory. The validation procedure is repeated until the index j reaches the number of comparisons to execute. It can be stopped at any time if a saved set of data does not correspond to its potentially associated reference model. In this case, the step S112 is executed. Storing the signals is not mandatory for the mechanical actions or the silences. Comparison can be made effectively on signals in real time to avoid excessive storing of data in memory.

For matters of power consumption saving, the data comparison is performed individually, for each mechanical action, in order to reduce the data to be processed, and thus the calculation resources and time needed by the control unit for the mathematical comparison. However, the reference model stored in memory can correspond to the entire pattern of data of a predetermined code of mechanical actions. In this case, the index j in the block diagram of FIG. 11 is not used and the second procedure is executed one time.

Figure 9:
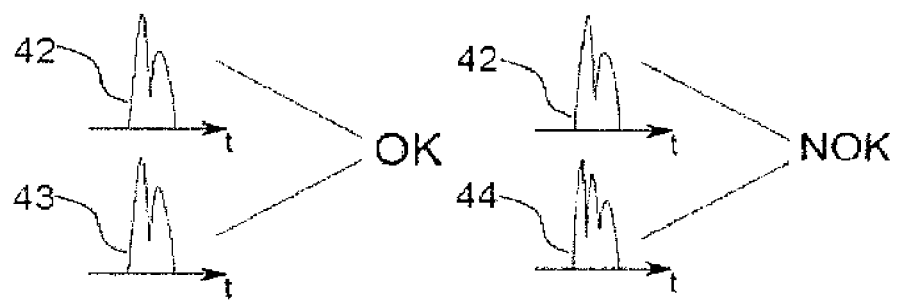
FIG. 9 illustrates the mechanical action signal measured by the sensor unit comparison with a reference signal in two cases. This corresponds to the second step of the code detection. In the first case (left side of the figure) the signal is similar, this step is thus validated (notation OK). In the other case (right side of the figure), the signal is not considered as similar to the reference signal, the step is therefore not validated (notation NOK).

FIG. 9 depicts an example of signals comparison of one mechanical action. The signals illustrated are a processed accelerometer signal output measured according to the hardware configuration represented in FIG. 5 along the Z axis. The signal is the envelope of the raw signal band-pass filtered and rectified. In the example, the comparison is performed on the base of shape parameters of the signal. The reference signal model 42 stored in memory is compared in a first case to the measured and processed signal 43 previously saved. A similarity index can be determined between the command signal and the reference signal. The shape parameters of both signals correspond in this case (i.e. the similarity index is greater than a determined threshold value) (notation OK); the measured signal 43 is validated in the steps S107 and S108 of the detection procedure (FIG. 11). In the second case, the signal model 42 is compared to the measured and processed signal 44 previously saved. In this case, the shape parameters do not correspond (i.e. the similarity index is less than a determined threshold value) (notation NOK). Step S107 is not validated. The detection is aborted and the data measured as well as parameters related to this detection are erased in step S112 and the procedure is repeated from step S101.

The comparison functions are implemented in the control unit. They are mathematical functions which allow validating similarities of several sets of data. In preferred embodiments, global shapes of signals are compared with mathematical functions such as normalized least mean squares or normalized inter-correlation functions which both take into account the shape of the signals for comparison. Methods such as dynamic time warping may also be used in order to offer a time tolerance on the reference model and the signal to compare. In fact, if the signal is dilated in time or compressed, the dynamic time warping method can consider the overall shape of the signal even if this shape is expanded or compressed in time relative to the reference model. In a further preferred embodiment, the comparison parameters can be others than shape parameters. Frequency and time characteristics combined or not combined with amplitude, statistical data or shape characteristics may also be employed to proceed to the comparison of a pattern of processed signal to a pre-stored reference model of signal characteristics. It has to be understood that the purpose of this phase, described in FIG. 11 in steps S107 and S108 is to determine if the signature of the signal measured, processed and saved in memory, corresponds to the actual reference signature pre-stored in memory in order to know if it corresponds to the expected mechanical action (or else to an expected silence, where necessary).

It has to be noted that during the detection phase, the system can still measure activity on the sensor(s).

It is important to note that the case presented above is only an example. It may be different as long as the method consists of detection of a code of mechanical actions with a predetermined rhythm and number of predetermined actions, combined with identification of each mechanical action signature and supplemental information in aim to validate the order issued by a user.

Figure 10:
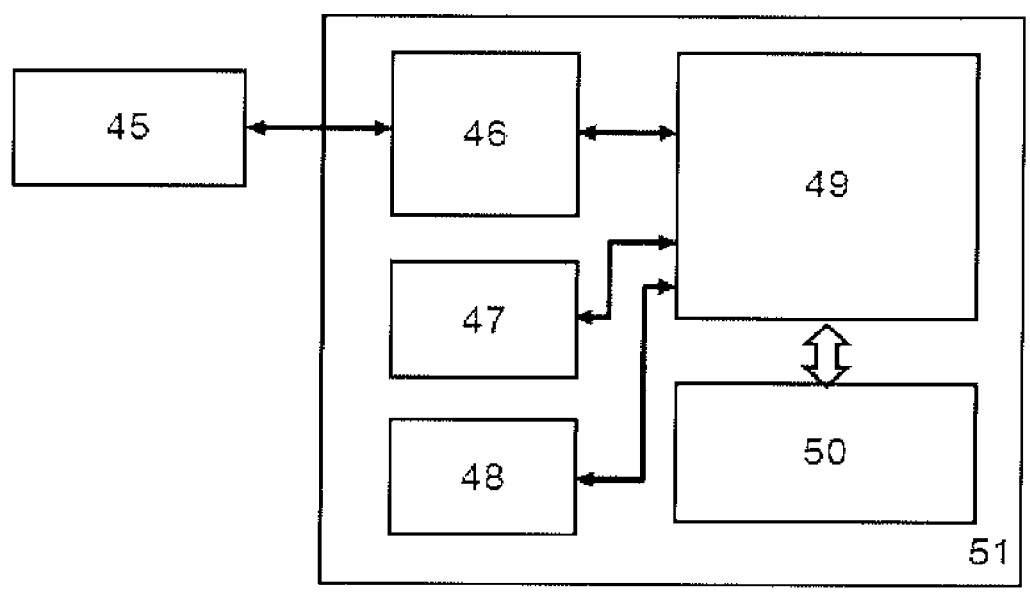
FIG. 10 is a block level diagram of the control circuit. The functions used for the detection of the code are described in this figure.

In FIG. 10, the hardware functions needed to implement the detection method described in the present invention are presented. In FIG. 10, the control unit is the control circuit 51 of the implantable device. The sensor interface 46 allows acquiring the data coming from the sensor unit 45 which can be composed of several sensors. The block 49 is the processing unit. It can be a digital controller or a microprocessor. Its function is to perform signal processing, mathematical treatment, communication with the other blocks and data handling. Timers 48 and memory 47 are also used for the treatment of the data. When a code is validated, the processing unit 49 sends the associated order to the targeted function included in the block 50.

The device may be equipped with a telemetry system in order to provide a configuration of the detection method. Sensitivity, tolerances, predetermined codes and orders may be some parameters which can be configured with an external wireless system communicating with the control unit.

When an order is validated, a feedback such as vibration or audible signal may be generated by the implantable device in order to warn the patient or an external person of the validation of an order.

In order to cancel an order, after executing the code to cancel, the user may perform the associated mechanical actions of the code several times very quickly. For example, the present invention may be employed in an artificial urinary sphincter using an accelerometer to measure abdominal skin tapping control. In order to avoid the micturition after executing the predetermined code, the patient may tap several times quickly on the abdomen, where the implant is located, which may send this order to the control unit of the instantaneous closing of the occlusive cuff.

One of the major constraints in active implantable devices is power consumption. In order to avoid continuously supplying the sensor(s), one of the sensors or the sensor can be a device which can generate an electrical signal without the need to be supplied by an electrical source. For instance, a sensor may be designed with piezoelectric or electromagnetic materials in order to generate an electrical signal when a mechanical action is applied on the sensor. FIG. 12 shows a preferred but not limited configuration comprising one 3-axis accelerometer 9 and one piezoelectric vibration sensor. The piezoelectric sensor is made of a seismic mass 52 suspended by a flexible structure 54 attached to the rigid structure 53 secured on the implantable device. A piezoelectric layer on the flexible structure 54 is used to generate an electrical signal when the flexible structure is bended by seismic movements generated by external vibrations. The electrical signal generated is then used to wake up the control unit 5 (for instance by using a pin interruption) and the 3-axis accelerometer, both previously in a sleep mode in order to minimize the electrical power consumption. The detection procedure of predetermined code of mechanical actions is then processed as described in the present invention. When the detection phase is done, the control unit and the 3-axis accelerometer go back to a sleep mode.

An external device may be used in order to generate the predetermined code of mechanical actions. For example, a mobile phone with an application controlling the vibrator may generate a vibration on the skin of the patient, in the implantation area. In the case of detection by an accelerometer, the code made of vibrations and silences may then be detected by the system implanted into the patient's body.

The invention claimed is:

1. A system for controlling a device implanted in an animal or human body, on the basis of commands issued by a user comprising:
   at least one sensor adapted for measuring mechanical actions exerted voluntarily by the user on or in the body in which the device is implanted,
   a control unit comprising a microprocessor and being configured to:
   process at least one signal coming from said sensor,
   detect a predetermined code issued by the user in said signal, according to a pattern comprising at least one mechanical action and at least one supplemental information detectable by said at least one sensor,
   identify each mechanical action and each supplemental information measured in a portion of said signal;
   compare characteristics of each portion of said signal with a corresponding reference model of the signal characteristics, the control unit comprising a memory in which is stored at least one reference model of said signal characteristics,
   determine, from said signal comparison, whether said at least one measured mechanical action and said at least one supplemental information actually belong to said predetermined code, and
   send a predetermined order to said implanted device if the applied pattern corresponds to the predetermined code,
   wherein said sensor and said control unit are implanted in said animal or human body, and said mechanical actions are exerted voluntarily by the user on or in the animal or human body in which the device is implanted.

2. The system according to claim 1, wherein said at least one sensor and said control unit are adapted for the detection of a predetermined posture taken by said animal or human body during a predetermined duration corresponding to said supplemental information.

3. The system according to claim 1, wherein said microprocessor comprises means for measuring and detecting the duration of each detectable supplemental information and of each mechanical action.

4. The system according to claim 1, wherein the microprocessor is further configured to:
   a) detect said supplemental information in a portion of said signal that has a level below a predetermined threshold during a period having a duration comprised between a minimum and a maximum,
   b) detect said mechanical action in a portion of said signal that has a level above a predetermined threshold during a period having a duration comprised between a minimum and a maximum mechanical action after a supplemental information,
   c) store characteristics of said signal in a memory, d) repeat steps (a) to (c) for each portion of said signal until the end of the pattern, e) if said pattern does not correspond to said predetermined code, restart to step (a) at any time until detecting a pattern corresponding to said predetermined code.

5. The system according to claim 1, wherein said predetermined order to send to the implanted device is selected from the group consisting of an activation or deactivation of said implanted device, an activation or deactivation of at least one function of said implanted device, a modification of at least one parameter of said implanted device, a modification of a therapy provided by said implanted device, a modification of the shape of said implanted device, and an activation or deactivation of a feature of at least one safety of said implanted device.

6. The system according to claim 1, wherein said system comprises means for generating a feedback for the user when said predetermined order is sent to said implanted device.

7. The system according to claim 1, wherein said at least one sensor measures the mechanical action selected from the group consisting of an external manual percussion on the body, over the implantation site of said sensor, a muscular contraction, vibrations, a pressure increase of a body cavity and a pressure increase on the skin over the implantation site of said sensor.

8. The system according to claim 1, wherein said controlled implanted device is an artificial sphincter and in that said predetermined order comprises opening or closing an occlusive element of said artificial sphincter.

9. The system according to claim 1, wherein said system comprises means for periodically updating said reference model(s).

10. The system according to claim 1, wherein at least two different predetermined codes are stored into said memory, each of this codes, when applied to the body, leading to the sending of an associated specific order to the implanted device.

11. The system according to claim 1, further comprising a wireless communication system between the implantable device and an external wireless base in order to configure the detection parameters of the predetermined codes detection.

12. The system according to claim 1, wherein said at least one sensor is selected from the group consisting of a 1-, 2- or 3-axis accelerometer, a gyroscope, a localization system, a pressure sensor and an electric commutator.

13. The system according to claim 1, wherein said sensor is not electrically supplied and generates at least one electrical signal when a mechanical action is applied on said sensor.

14. An implantable device adapted to be implanted in an animal or human body, comprising a control system according to claim 1.

15. The implantable device according to claim 14, consisting of an artificial sphincter.

16. A method for detection of an activation command of a device implanted in an animal or human body by a user, comprising:

receiving from at least one sensor of the device a signal comprising a sequence of values, some of said values being representative of mechanical actions exerted voluntarily by the user on or in the animal or human body in which the device is implanted and other of said values being representative of supplemental information, processing said signal coming from said at least one sensor, detecting a predetermined code issued by the user in said signal, according to a pattern comprising at least one mechanical action and at least one supplemental information detectable by said at least one sensor, identifying each mechanical action and each supplemental information measured in a portion of said signal;

receiving at least one reference model of characteristics of said signal from a memory of the device, comparing characteristics of each portion of said signal with the reference model, determining, from said signal comparison, whether said at least one measured mechanical action and said at least one supplemental information belong to said predetermined code, and if the similarity index is greater than a threshold value, recognition of a predetermined activation code of the device sending a predetermined order to said implanted device if the applied pattern corresponds to the predetermined code.

17. The method according to claim 16, wherein the values representative of supplemental information comprise a period between two successive mechanical actions exerted on the at least one sensor.

18. A system for controlling a device implanted in an animal or human body, on the basis of commands issued by a user comprising:

at least one sensor adapted for measuring mechanical actions exerted voluntarily by the user on or in the body in which the device is implanted, a control unit comprising a microprocessor and being configured to:

process at least one signal coming from said sensor, detect a predetermined code issued by the user in said signal, according to a pattern comprising at least one mechanical action and at least one supplemental information detectable by said sensor(s), identify each mechanical action and each supplemental information measured in a portion of said signal;

compare characteristics of each portion of said signal with a corresponding reference model of the signal characteristics, the control unit comprising a memory in which is stored at least one reference model of said signal characteristics, determine, from said signal comparison, whether said at least one measured mechanical action and said at least one supplemental information actually belong to said predetermined code, and send a predetermined order to said implanted device if the applied pattern corresponds to the predetermined code, wherein said sensor and said control unit are implanted in said animal or human body, wherein said at least one sensor measures the mechanical action selected from the group consisting of an external manual percussion on the body, over the implantation site of said sensor, a muscular contraction, vibrations, a pressure increase of a body cavity and a pressure increase on the skin over the implantation site of said sensor.

* * * * *